United States Patent [19]

Chen

[11] Patent Number: 5,436,066
[45] Date of Patent: Jul. 25, 1995

[54] ABSORBENT COMPOSITION INCLUDING A MICROFIBER

[75] Inventor: Franklin M. C. Chen, Appleton, Wis.

[73] Assignee: Kimberly-Clark Corporation, Neenah, Wis.

[21] Appl. No.: 176,624

[22] Filed: Dec. 30, 1993

[51] Int. Cl.[6] .............................................. D04H 1/58
[52] U.S. Cl. ................................ 428/288; 427/213; 428/284; 428/297; 428/326; 428/903; 428/913; 604/358
[58] Field of Search ............... 428/288, 903, 913, 284, 428/297, 326; 427/213; 604/358

[56] References Cited

U.S. PATENT DOCUMENTS

3,901,236  8/1975  Assarsson et al. ............... 128/284

Primary Examiner—James J. Bell
Attorney, Agent, or Firm—John R. Schenian

[57] ABSTRACT

Disclosed is an absorbent composition including a hydrogel-forming polymeric material and a microfiber; disposable absorbent products, including the absorbent composition, intended for the absorption of body liquids; and a method for preparing the absorbent composition.

47 Claims, 4 Drawing Sheets

ABSORBENT COMPOSITION INCLUDING A MICROFIBER

BACKGROUND OF THE INVENTION

1. Field of the Invention

The present invention relates to an absorbent composition including a hydrogel-forming polymeric material and a microfiber; disposable absorbent products, including the absorbent composition, intended for the absorption of body liquids; and a process for preparing the absorbent composition.

2. Description of the Related Art

The use of hydrogel-forming polymeric materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials have been described for use as hydrogel-forming polymeric materials in such personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile.

It is also known to combine a hydrogel-forming polymeric material with other materials by various methods in order to enhance the absorbent or other properties of the hydrogel-forming polymeric material. One method of preparing an absorbent composition, for example, comprises blending a hydrogel-forming polymeric material and fibers.

Unfortunately, many mechanical methods of treating or preparing an absorbent composition comprising a hydrogel-forming polymeric material result in the absorbent properties of the hydrogel-forming polymeric material being negatively affected. For example, many known hydrogel-forming polymeric materials are single particles or agglomerations of fine particles. When such materials are treated by mechanical methods such as blending, the particles or agglomerations are typically shattered or broken apart, which negatively affects the absorbent properties of the hydrogel-forming polymeric material.

SUMMARY OF THE INVENTION

The present invention concerns an efficient and effective manner for preparing an absorbent composition comprising a hydrogel-forming polymeric material and a microfiber wherein the morphology of the hydrogel-forming polymeric material is substantially maintained during the preparation such that the absorbent properties of the hydrogel-forming polymeric material are substantially maintained.

One aspect of the present invention concerns an absorbent composition comprising a hydrogel-forming polymeric material and a microfiber.

One embodiment of such an absorbent composition comprises from about 80 to less than 100 weight percent of a hydrogel-forming polymeric material and from about 20 to greater than 0 weight percent of a microfiber, wherein all weight percents are based on the total weight of the hydrogel-forming polymeric material and the microfiber in the absorbent composition; wherein the microfiber has a surface area between about 10 to about 25 square meters per gram, a static charge between about $-30$ to about $-300$ volts, a fiber length to diameter ratio of at least about 50 to 1, and wherein the microfiber is attached to the hydrogel-forming polymeric material; and wherein the absorbent composition exhibits a Capillary Tension Capacity value, at a negative pressure gradient of about 15 centimeters, that is at least about 50 percent greater than the Capillary Tension Capacity value exhibited by an otherwise identical absorbent composition which does not comprise the microfiber.

In another aspect, the present invention concerns a disposable absorbent product for the absorption of liquids such as body liquids.

One embodiment of such a disposable absorbent product comprises a liquid-permeable topsheet, a backsheet, and an absorbent structure positioned between the topsheet and the backsheet, wherein the absorbent structure comprises an absorbent composition comprising a hydrogel-forming polymeric material and a microfiber.

In another aspect, the present invention concerns a process for preparing an absorbent composition comprising a hydrogel-forming polymeric material and a microfiber.

One embodiment of such a process comprises using a fluidized bed to contact a hydrogel-forming polymeric material and a microfiber to form an absorbent composition.

DETAILED DESCRIPTION OF THE PREFERRED EMBODIMENTS

One aspect of the present invention concerns an absorbent composition comprising a hydrogel-forming polymeric material and a microfiber.

As used herein, "hydrogel-forming polymeric material" is meant to refer to a high-absorbency material commonly referred to as a superabsorbent material. Such high-absorbency materials are generally capable of absorbing an amount of a liquid, such as water, synthetic urine, a 0.9 weight percent aqueous saline solution, or body liquids such as menses, urine, or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions such as about 23° C. and about 30 to about 60 percent relative humidity. Upon absorption of the liquid, the superabsorbent material typically swells and forms a hydrogel.

The superabsorbent material may be formed from an organic hydrogel material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines. Other suitable hydrogel polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water-insoluble yet water-swellable. Crosslinking may, for example, be by irradiation or covalent, ionic, van der Waals, or hydrogen bonding. Suitable superabsorbent materials are typically available from various commercial vendors, such as The Dow Chemical Company, Hoechst Celanese, Allied Colloids Limited, or Stockhausen, Inc.

The hydrogel-forming polymeric material employed in the absorbent articles of the present invention suitably should be able to absorb a liquid under an applied load. For the purposes of this application, the ability of a hydrogel-forming polymeric material to absorb a liquid under an applied load and thereby perform work is quantified as the Absorbency Under Load (AUL) value. The AUL value is expressed as the amount (in grams) of an aqueous 0.9 weight percent sodium chloride solution which the hydrogel-forming polymeric material can absorb per gram of hydrogel-forming polymeric material under a load of about 0.3 pound per square inch (approximately 2.0 kilopascals) while restrained from swelling in the plane normal to the applied load. The hydrogel-forming polymeric material employed in the absorbent structures of the present invention suitably exhibits an AUL value of at least about 15, more suitably of at least about 20, and up to about 50. The method by which the AUL value may be determined is set forth, for example, in detail in U.S. Pat. No. 5,149,335 or U.S. Pat. No. 5,247,072, incorporated herein by reference.

Suitably, the hydrogel-forming polymeric material is in the form of particles which, in the unswollen state, have maximum cross-sectional diameters within the range of from about 50 microns to about 1000 microns, preferably within the range of from about 100 microns to about 800 microns, as determined by sieve analysis according to American Society for Testing and Materials (ASTM) test method D-1921. It is understood that the particles of hydrogel-forming polymeric material falling within the ranges described above may comprise solid particles, porous particles, or may be agglomerated particles comprising many smaller particles agglomerated into particles falling within the described size ranges.

The hydrogel-forming polymeric material is present in the absorbent composition of the present invention in an amount effective to result in the absorbent composition being able to absorb a desired amount of liquid under desired conditions. The hydrogel-forming polymeric material is beneficially present in the absorbent composition of the present invention in an amount of from about 80 to less than 100 weight percent, suitably from about 85 to about 99 weight percent, and more suitably from about 85 to about 95 weight percent, based on the total weight of the hydrogel-forming polymeric material and the microfiber in the absorbent composition.

It has been discovered that by combining the hydrogel-forming polymeric material with a microfiber in an absorbent composition, it is possible to achieve enhanced absorbent properties as compared to using either the hydrogel-forming polymeric material or the microfiber separately.

A wide variety of natural and synthetic fibers can be employed in the preparation of the absorbent composition of the present invention. Illustrative fibers include, but are not limited to, wood and wood products, such as wood pulp fibers, cellulose flocs, cotton linter flocs and the like, inorganic fibers, synthetic fibers such as nylon flocs, rayon flocs and the like. Fibers beneficially used in the present invention include polyacrylonitrile fibers and cellulose acetate fibers.

It is also possible to use mixtures of one or more natural fibers or one or more synthetic fibers, or combinations of the two. Preferred fibers are those which are hydrophilic in nature. However, hydrophobic fibers can also be used. It is possible to treat the fiber surfaces by an appropriate method to render them more or less hydrophilic. When surface treated fibers are employed, the surface treatment is desirably nonfugitive; that is, the surface treatment desirably does not wash off the surface of the fiber with the first liquid insult or contact. For the purposes of this application, a surface treatment on a generally hydrophobic polymer will be considered to be nonfugitive when a majority of the fibers demonstrate a liquid in air contact angle of less than 90° for three consecutive contact angle measurements, with drying between each measurement; that is, the same fiber is subjected to three separate contact angle determinations and, if all three of the contact angle determinations indicate a contact angle of liquid in air of less than 90°, the surface treatment on the fiber will be considered to be nonfugitive. If the surface treatment is fugitive, the surface treatment will tend to wash off of the fiber during the first contact angle measurement, thus exposing the hydrophobic surface of the underlying fiber, and will demonstrate subsequent contact angle measurements greater than 90°. Beneficial wettability agents include polyakylene glycols such as polyethylene glycols. The wettability agent is used in an amount comprising beneficially less than about 5 weight percent, suitably less than about 3 weight percent, and more suitably less than about 2 weight percent, of the total weight of the absorbent composition being treated.

As used herein, the term "wettable" is meant to refer to a fiber which exhibits a liquid, such as water, synthetic urine, or a 0.9 weight percent aqueous saline solution, in air contact angle of less than 90°. As used herein, the contact angle may be determined, for example, as set forth by Robert J. Good and Robert J. Stromberg, Ed., in "Surface and Colloid Science—Experimental Methods", Vol. 11, (Plenum Press, 1979). Suitably, a wettable fiber refers to a fiber which exhibits a synthetic urine in air contact angle of less than 90° at a temperature between about 0° C. and about 100° C. and suitably at ambient conditions, such as about 23° C.

Beneficially, the microfibers useful in the present invention have a surface area between about 10 to about 25 square meters per gram of microfiber. Suitably, the microfibers useful in the present invention have a surface area between about 15 to about 25 square meters per gram of microfiber. More suitably, the microfibers useful in the present invention have a surface area between about 18 to about 22 square meters per gram of microfiber. The surface area of the microfibers may be measured, for example, by the B.E.T. nitrogen adsorption method known to those skilled in the art.

Beneficially, the microfibers useful in the present invention have a static charge between about $-30$ to about $-300$ volts. Suitably, the microfibers useful in the present invention have a static charge between about $-50$ to about $-250$ volts. More suitably, the microfibers useful in the present invention have a static charge between about $-60$ to about $-230$ volts. As used herein, the use of a negative sign $(-)$ in regard to the static charge is meant to refer to a negative charge. The static charge of the microfiber may be measured by electrostatic measurement means known to those skilled in the art. While not wishing to be bound by any particular theory, it is believed that a static charge on the microfibers assists in the attracting and adhering of the microfibers to the hydrogel-forming polymeric material, particularly when the absorbent composition is prepared using a fluidized bed.

Beneficially, the microfibers useful in the present invention have a length of less than about 1 millimeter. Suitably, the microfibers useful in the present invention have a length of less than about 0.5 millimeter. More suitably, the microfibers useful in the present invention have a length of less than about 0.3 millimeter.

Beneficially, the microfibers useful in the present invention have a diameter of less than about $5 \times 10^{-6}$ meter. Suitably, the microfibers useful in the present invention have a diameter of less than about $1 \times 10^{-6}$ meter. More suitably, the microfibers useful in the present invention have a diameter of less than about $5 \times 10^{-7}$ meter.

Beneficially, the microfibers useful in the present invention have a length to diameter ratio of at least about 50 to 1. Suitably, the microfibers useful in the present invention have a length to diameter ratio of at least about 200 to 1. More suitably, the microfibers useful in the present invention have a length to diameter ratio of at least about 400 to 1.

While not wishing to be bound by any particular theory, it is believed that the microfibers attached to the hydrogel-forming polymeric material aid in entrapping or constraining a liquid and conducting the liquid by capillary action to surround, as well as to the surface of, the hydrogel-forming polymeric material where the liquid may be absorbed by the hydrogel-forming polymeric material.

Also, those microfibers which partially extend from the hydrogel-forming polymeric material surface can serve to constrain the absorbent composition in an absorbent structure such as a fibrous matrix.

The microfibers are present in the absorbent composition of the present invention in an amount effective to result in the absorbent composition exhibiting improved absorbent distribution properties. Beneficially, the microfibers are present in the absorbent composition of the present invention in an amount of from greater than 0 to about 20 weight percent, more beneficially from about 1 to about 15 weight percent, and suitably from about 5 to about 15 weight percent, based on total weight of the hydrogel-forming polymeric material and the microfibers in the absorbent composition.

Typically, the lower limit of the amount of microfibers that are to be used in the absorbent composition is determined by how well the microfibers can be homogeneously mixed and contacted with the hydrogel-forming polymeric material. A more uniform dispersal of the microfibers will typically result in fewer of the microfibers being needed in order to achieve an effective and efficient incorporation of the absorbent composition into an absorbent structure in a disposable absorbent product as compared to where the microfibers are not as uniformly dispersed within the absorbent composition. In addition, the upper and lower limits of the amount of microfibers that are to be used in the absorbent composition may be affected by the nature of the microfibers. Generally speaking, one would like to use as little of the microfibers as possible.

When the absorbent compositions of the present invention are used in a disposable absorbent structure or product, it will generally be desirable that the absorbent composition does not detract from the aesthetic appearance of the disposable absorbent structure or product. Thus, it will generally be desirable to use an absorbent composition that has a generally white or clear color. As such, it may be desirable to use microfibers that have a generally white or clear color.

Beneficially, the absorbent composition of the present invention comprising a hydrogel-forming polymeric material and microfibers exhibits a specific gravity of less than about 0.1. Suitably, the absorbent composition of the present invention exhibits a specific gravity of less than about 0.05. More suitably, the absorbent composition of the present invention exhibits a specific gravity of less than about 0.02.

The absorbent composition of the present invention, comprising a hydrogel-forming polymeric material and microfibers, exhibits a Capillary Tension Capacity value, at a negative pressure gradient of about 15 centimeters, as defined and described in the Test Methods sections herein, beneficially of at least about 10 grams, suitably of at least about 15 grams, and more suitably of at least about 17 grams of liquid per gram of absorbent composition.

The absorbent composition of the present invention, comprising a hydrogel-forming polymeric material and microfibers, exhibits a Capillary Tension Capacity value, at a negative pressure gradient of about 15 centimeters, that is beneficially at least about 50 percent greater, suitably at least about 100 percent greater, and more suitably at least about 200 percent greater, than the Capillary Tension Capacity value exhibited by an otherwise identical absorbent composition which does not comprise the microfiber.

The absorbent composition of the present invention, comprising a hydrogel-forming polymeric material and microfibers, exhibits a Liquid Uptake Rate value, as defined and described in the Test Methods section herein, that is beneficially at least about 50 percent greater, suitably at least about 100 percent greater, and more suitably at least about 200 percent greater than the Liquid Uptake Rate value exhibited by an otherwise identical absorbent composition which does not comprise the microfiber.

The absorbent composition of the present invention, comprising a hydrogel-forming polymeric material and microfibers, exhibits an Absorbency Under Load value, as defined and described in the Test Methods section herein, that is beneficially at least about 10 percent greater, suitably at least about 25 percent greater, and more suitably at least about 50 percent greater than the Absorbency Under Load value exhibited by an otherwise identical absorbent composition which does not comprise the microfiber.

The hydrogel-forming polymeric material and the microfibers may generally be mixed or combined in any acceptable manner in order to prepare the absorbent composition of the present invention as long as the absorbent composition exhibits the desired absorbent and other properties described herein.

Figure 2:
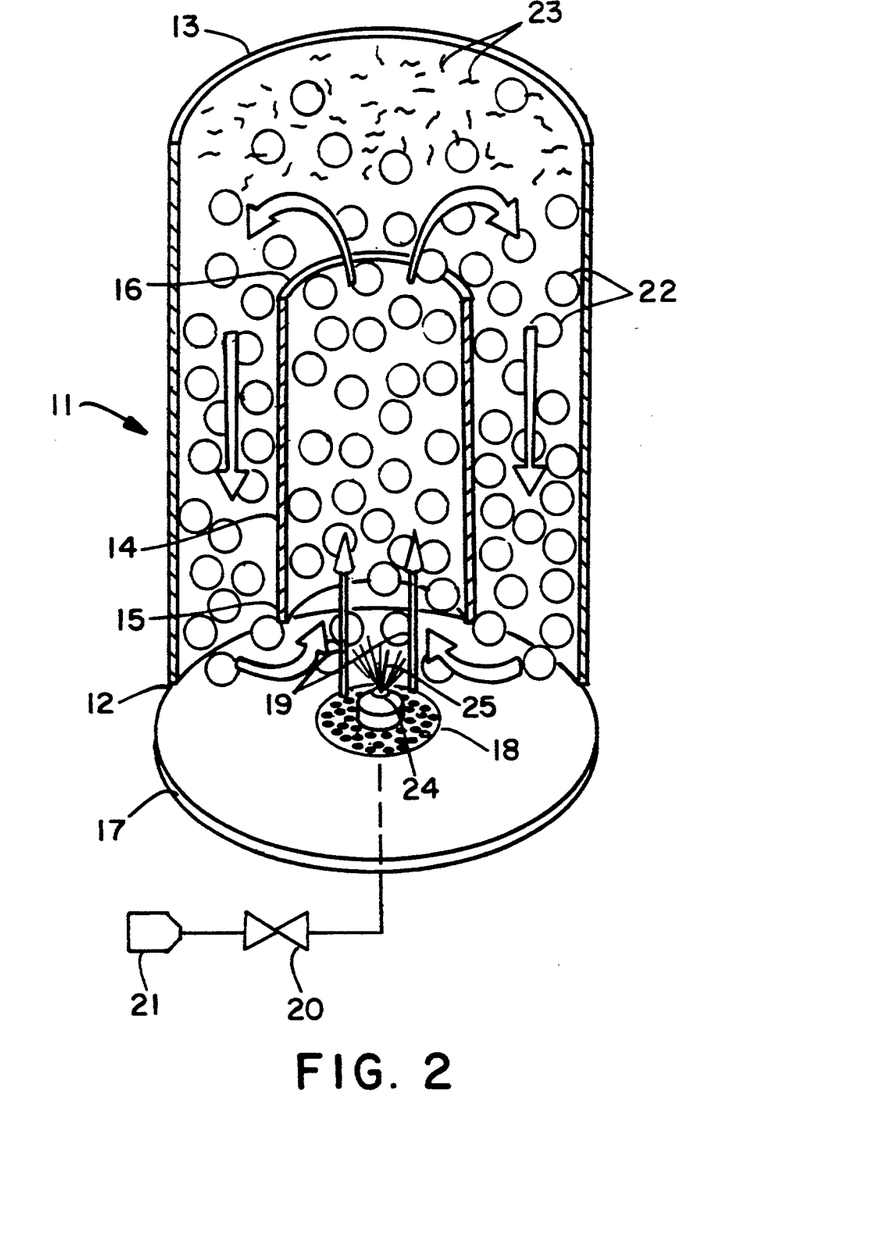
FIG. 2 illustrates a schematic view of a representative apparatus useful in the present invention.

Beneficially, a fluidized bed process is used to contact the hydrogel-forming polymeric material and the microfibers. Referring to FIG. 2, a generally vertically-mounted, generally cylindrical chamber 11 is open at chamber proximal end 12 and closed at chamber distal end 13. The chamber 11 is provided with an inner chamber 14 that has a diameter less than that of chamber 11. Inner chamber 14 is open at both inner chamber proximal end 15 and inner chamber distal end 16. Chamber proximal end 12 is fitted with a plate 17 that has a porous area 18 that generally matches the diameter of inner chamber 14. Inner chamber 14 is positioned a distance above plate 17 and is generally aligned along the vertical axis of chamber 11. Through porous area 18 is provided an upward flowing air stream 19 such as from a valve 20 from a source of compressed air 21. The upward flowing air stream 19 generally flows through inner chamber 14 by entering through inner chamber proximal end 15 and exiting through inner chamber distal end 16. Into the chamber 11 are placed hydrogel-forming polymeric material 22 and microfibers 23. The upward flowing air stream 19 is adjusted so as to provide a fluid-like flow to the hydrogel-forming polymeric material 22 and microfibers 23. With a properly adjusted air stream 19, the relatively lighter microfibers 23 will generally float on the surface of the air flow near chamber distal end 13. The relatively heavier hydrogel-forming polymeric material 22 will generally be carried upward through inner chamber distal end 16, make contact with the microfibers 23 floating near chamber distal end 13, sink back down to plate 17, and continue in a cyclic flow pattern by being carried upward again through inner chamber 14. When contact is made between the hydrogel-forming polymeric material 22 and microfibers 23, the microfibers 23 will become attached to the hydrogel-forming polymeric material 22 by means of entanglement or adhesion to form the absorbent composition of the present invention. In order to aid in the attachment of the microfibers 23 to the hydrogel-forming polymeric material 22, an adhesive sprayer means 24 may be positioned near the center of the plate 17 so that the hydrogel-forming polymeric material 22 is coated with an adhesive material 25 as it enters the inner chamber 14 during its cyclic flow. Alternatively, or in addition to the adhesive sprayer means 24, an additional sprayer means (not shown) may be provided to coat the hydrogel-forming polymeric material 22 with a wettability agent. The cyclic flow of the absorbent composition is generally allowed to continue until a desired amount of the microfibers 23 have been contacted with the hydrogel-forming polymeric material 22. The absorbent composition is then recovered or removed from the chamber 11.

It has been found that when a fluidized bed process is used to prepare the absorbent composition of the present invention, the absorbent composition exhibits superior absorbent properties as compared to an identical absorbent composition that is not prepared using a fluidized bed process but, for example, is prepared using a blending process.

A fluidized bed process is relatively mild in its effect on the hydrogel-forming polymeric material being contacted with the microfibers and is therefore less damaging to the microstructure of the hydrogel-forming polymeric material as compared to other processes. In addition, the use of a fluidized bed process allows for the more effective and efficient application of other materials to the absorbent composition, such as adhesives or surface treatments such as for wettability.

Beneficially, the absorbent composition of the present invention exhibits improved absorbent properties, such as Capillary Tension Capacity values and Liquid Uptake Rate values, when prepared using a fluidized bed process as compared to using a blending process.

Other methods of mixing or combining the magnetically-responsive material and the hydrogel-forming polymeric material will be readily apparent to those skilled in the art.

The absorbent compositions according to the present invention are suited to absorb many liquids, such as water, saline, synthetic urine, and body liquids such as urine, menses, and blood, and are suited for use in disposable absorbent products such as diapers, adult incontinent products, and bed pads; in catamenial devices such as sanitary napkins, and tampons; and in other absorbent products such as wipes, bibs, wound dressings, and surgical capes or drapes. Accordingly, in another aspect, the present invention relates to a disposable absorbent product comprising an absorbent composition as described herein.

Use of the described absorbent compositions in disposable absorbent products allows for the formation of a disposable absorbent product which is able to rapidly receive a discharged liquid and yet which product is thin. Typically, the absorbent composition will be incorporated into a disposable absorbent product in the form of an absorbent structure. Such disposable absorbent products generally comprise a liquid-permeable topsheet, a backsheet, and an absorbent structure, such as an absorbent structure comprising the absorbent composition of the present invention, located between the topsheet and backsheet.

Absorbent structures for incorporating an absorbent composition into a disposable absorbent product are generally well known. An absorbent structure may take the form, for example, of a batt of comminuted wood pulp fluff, a tissue layer, or of a web structure comprising an entangled fibrous mass formed, for example, from an extruded thermoplastic composition. Suitably, the absorbent structure is formed so as to constrain or entrap the absorbent composition within its structure. The absorbent composition may be incorporated into the absorbent structure either during or after the formation of the general form of the absorbent structure.

The microfibers attached to the hydrogel-forming polymeric material in the absorbent composition of the present invention are believed to assist in constraining the absorbent composition in an absorbent structure such as a fibrous matrix. As such, an absorbent structure comprising the absorbent composition of the present invention will exhibit less loss of the absorbent composition when evaluated using a shake test as compared to an absorbent structure comprising an otherwise identical absorbent composition which does not comprise the microfiber. An absorbent structure comprising the absorbent composition of the present invention will beneficially exhibit a 50 weight percent, suitably a 75 weight percent, and more suitably a 90 weight percent, lower loss of the absorbent composition when evaluated using a shake test as compared to an absorbent structure comprising an otherwise identical absorbent composition which does not comprise the microfiber.

Exemplary disposable absorbent products are generally described in U.S. Pat. No. 4,710,187; U.S. Pat. No. 4,762,521; U.S. Pat. No. 4,770,656; U.S. Pat. No. 4,798,603; and U.S. Ser. No. 08/096,654, filed Jul. 22, 1993 in the name of Hansen et al., which references are incorporated herein by reference.

In one embodiment of the present invention, a disposable absorbent product is provided, which disposable absorbent product comprises a topsheet, a backsheet, and an absorbent structure comprising a hydrogel-forming polymeric material and a microfiber, wherein the absorbent structure is positioned between the topsheet and the backsheet.

While one embodiment of the invention will be described in terms of the use of an absorbent composition in an infant diaper, it is to be understood that the absorbent composition is equally suited for use in other disposable absorbent products known to those skilled in the art.

Figure 1:
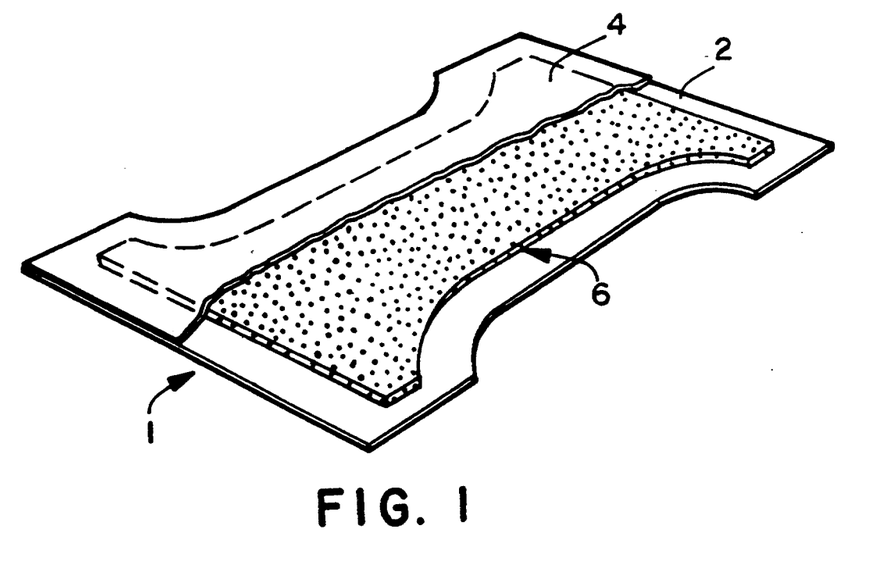
FIG. 1 represents a disposable diaper according to the present invention.

Turning now to the drawings, FIG. 1 illustrates a disposable diaper 1 according to one embodiment of the present invention. Disposable diaper 1 includes a backsheet 2, a topsheet 4, and an absorbent structure 6, located between the backsheet 2, and the topsheet 4. Absorbent structure 6 is an absorbent structure according to the present invention. Specifically, in the illustrated embodiment, absorbent structure 6 comprises an absorbent composition comprising a hydrogel-forming polymeric material and a microfiber.

Those skilled in the art will recognize materials suitable for use as the topsheet and backsheet. Exemplary of materials suitable for use as the topsheet are liquid-permeable materials such as spun-bonded polypropylene or polyethylene having a basis weight of from about 15 to about 25 grams per square meter. Exemplary of materials suitable for use as the backsheet are liquid-impervious materials such as polyolefin films, as well as vapor-pervious materials such as microporous polyolefin films.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Various methods may be used to incorporate an absorbent composition of the present invention into an absorbent structure or disposable absorbent product. For example, processes can be employed to produce selected mixtures and distributions of an absorbent composition into a filamentary or fibrous material during an airlaying or airforming operation.

Test Methods

Capillary Tension Capacity Test

The Capillary Tension Capacity (CTC) Test is a test which measures the ability of an absorbent material to absorb a liquid (0.9 weight percent solution of sodium chloride in distilled water) while under an applied load or restraining force while subjected to a negative pressure gradient.

Figure 3:
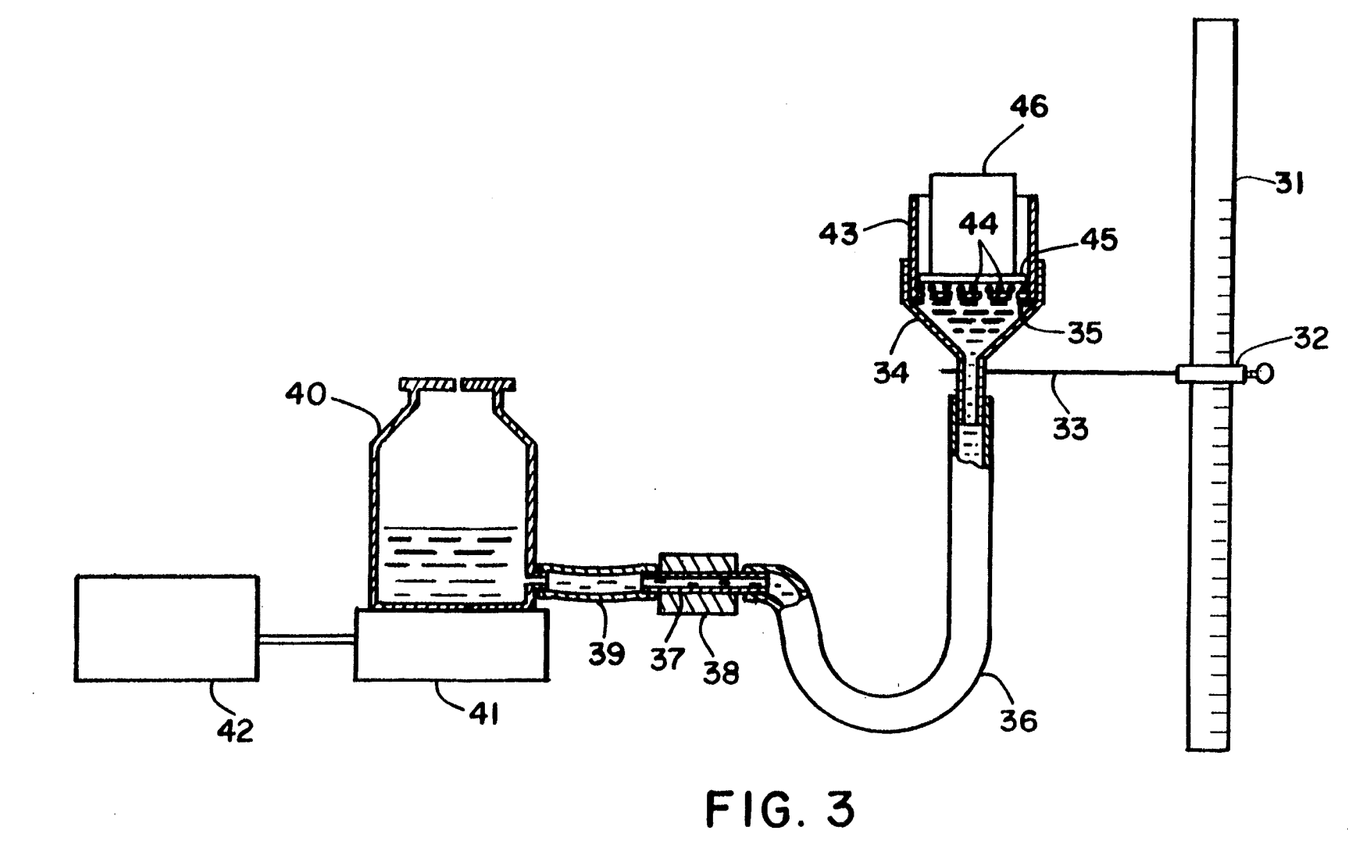
FIG. 3 is a side elevational view of an apparatus used to measure capillary tension capacity values of absorbent compositions at a negative pressure gradient and under an applied restraint.

Referring to FIG. 3, the apparatus and method for determining CTC values will be described. Shown is a perspective view of the apparatus in position during a test.

Shown is a laboratory stand 31 which is gradated in centimeters and which has an adjustable collar 32 for raising and lowering a support ring 33. The support ring 33 supports a funnel 34 which has a 6 centimeter diameter. In the funnel 34 is placed a porous glass plate 35 which has a nominal maximum pore diameter of about 40 to 60 micrometers. To the bottom of the funnel 34 is attached a first flexible plastic tubing 36 which is attached at its other end to a rigid plastic tube 37 which is held in place with a clamp 38. The other end of the rigid plastic tube 37 is attached to a second flexible plastic tubing 39 which is attached at its other end to a vented liquid reservoir 40. The vented liquid reservoir 40 rests on a balance 41 which is attached to a recorder 42 which is used to record the weight loss of liquid from the vented liquid reservoir 40 as liquid is absorbed by the sample being evaluated.

A plastic sample cup 43, which contains the superabsorbent material sample 44 to be tested, has a liquid-permeable bottom and rests on top of the porous glass plate 35 in the funnel 34. A weight 46 rests on top of a spacer disc 45 resting on top of the superabsorbent material sample.

The sample cup 43 consists of a plastic cylinder having a 1 inch inside diameter and an outside diameter of 1.25 inches. The bottom of the sample cup 43 is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

To carry out the test, a 0.160 gram-sample of the absorbent material 44, which has been sieved to a particle size between 300 and 600 microns, is placed into the sample cup. The sample is then covered with a plastic spacer disc 45, weighing 4.4 grams, which is slightly smaller than the inside diameter of the sample cup and serves to protect the sample from being disturbed during the test. A 100 gram weight 46 is then placed on top of the spacer disc, thereby applying a load of about 0.3 pound per square inch. The sample cup is placed on the porous glass plate 35.

A negative pressure gradient is established by lowering the funnel 34 until liquid from the vented liquid reservoir 40 flows through the tubing 37, 38, and 39 into the funnel 34 to make contact with the porous glass plate 35. The funnel 34 is then raised to a level along the gradated laboratory stand 31 until a desired negative pressure gradient (as measured in difference in height, in centimeters, between the top of the liquid level in the vented liquid reservoir 40 and the level of the porous glass plate 35) is established. The recorder is then allowed to measure the amount of liquid which is removed from the vented liquid reservoir 40 and absorbed by the absorbent material, on a gram of liquid absorbed per gram of absorbent material basis, over a period of time.

Absorbency Under Load

The Absorbency Under Load (AUL) is a test which measures the ability of an absorbent material to absorb a liquid (0.9 weight percent solution of sodium chloride in distilled water) while under an applied load or restraining force.

The apparatus and method for determining AUL values will be described. A laboratory jack having an adjustable knob for raising and lowering a platform is used. A laboratory stand supports a spring connected to a modified thickness meter probe which passes through the housing of the meter, which is rigidly supported by the laboratory stand. A plastic sample cup, which contains the superabsorbent material sample to be tested, has a liquid-permeable bottom and rests within a Petri dish which contains the saline solution to be absorbed. A weight rests on top of a spacer disc resting on top of the superabsorbent material sample.

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41) which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of about 0.3 pound per square inch. The sample cup is placed in the Petri dish on the platform of the laboratory jack raised up until it contacts the tip of the probe. The meter is zeroed. A sufficient amount of saline solution is added to the Petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value expressed as grams saline solution absorbed per gram of absorbent. If desired, the readings of the modified thickness meter can be continuously input to a computer (Mitutoyo Digimatic Miniprocessor DP-2 DX) to make the calculations and provide AUL readings. As a cross-check, the AUL value can also be determined by determining the weight difference between the sample cup before and after the test, the weight difference being the amount of solution absorbed by the sample.

Liquid Uptake Rate

As used herein, the "liquid uptake rate" is defined (in milliliters/second (mls/sec)) as the volume of liquid (in milliliters) used to insult an absorbent garment, absorbent structure or containment means containing superabsorbent material divided by the length of time (in seconds) required for the absorbent garment, absorbent structure or containment means to absorb the liquid insult. The volume of each of three equal liquid insults is set at about 25 percent of the absolute saturated liquid retention capacity of the material being tested. For example, each of three equal 60 milliliter insults (180 milliliters total) are used when the object to be tested has an absolute liquid saturated retention capacity of at least about 240 milliliter of room temperature ($-23°$ C.) synthetic urine. The liquid insults are applied to material in a localized area (about 1 square centimeter) at a rate of 15 milliliters per second, with a period, for example, of about minutes between each insult. The absorption time commences when the liquid insult initially contacts the surface of the object being tested and ends when the liquid can no longer be seen on the surface of the tested object.

The liquid uptake rate value is determined as follows. The object to be tested, suitably having a length of about 9 inches (about 23 cm) and a width of about 3 inches (about 8 cm), a moisture content of less than about 7 weight percent, and an absolute liquid saturated retention capacity of at least about 240 ml, is placed in a cradle-shaped specimen holder. The test object is placed in the cradle-shaped specimen holder with the back end of the test object about 6.5 inches (about 17 cm) from the back of the cradle-shaped specimen holder, and the front end of the test object about 4.5 inches (about 11 cm) from the front of the cradle-shaped specimen holder. A target zone is marked about 3.25 inches (about 8 cm) from the front end of the test object.

A nozzle having about a 3 millimeter diameter orifice is placed a distance of about ¼ inch (about 0.6 cm) away from the target zone at an angle of about 60° from a generally horizontal major face of the test object. The nozzle may be attached, for example, to a pump equipped with a pulse suppressor for ease of delivery of the fluid to the nozzle.

A first insult of synthetic urine is applied to the test object from the nozzle at an average rate of about 15 milliliters per second until about 60 milliliters has been applied. After 5 minutes another 60 milliliters is applied. After another 5 minutes a third 60 milliliter insult is applied.

The time for each 60 milliliter insult to be absorbed by the test object is recorded. Each 60 milliliter insult is divided by the time period for its absorption and is reported as the liquid uptake rate value (in mls/sec) for that insult.

The absolute liquid saturated retention capacity of the tested object may be determined, for example, as set forth in copending U.S. patent application, Ser. No. 08/157,802, filed Nov. 23, 1993, by Huntoon et al., the entire disclosure of which is herein incorporated by reference and relied upon.

EXAMPLE 1

An absorbent composition was prepared using a fluidized bed process. The fluidized bed chamber had a diameter of about 9 inches and a height of about 22 inches. A sodium polyacrylate in an amount of 3,800 grams, available from Hoechst Celanese Corporation, Narrows, Va., under the trade designation IM 5000P, was used as the hydrogel-forming polymeric material. Cellulose acetate fibers in an amount of 200 grams, having fiber lengths between about 20 to 200 micrometers, fiber diameters between about 0.5 to 5 micrometers, and surface areas of about 20 square meters per gram of fiber, and available from Hoechst Celanese Corporation, Narrows, Va., under the trade designation FIBRETS, was used as the microfiber.

The sodium polyacrylate and the cellulose acetate fibers are placed in the fluidized bed chamber and allowed to mix, at a temperature of about 140° F. (about 60° C.), for about 8.5 minutes. The air flow is run at a rate equivalent to an air duct pressure of about 0.27 inches of water.

A polyethylene glycol having a molecular weight of about 8,000, in an amount of about 45 grams, available from the Union Carbide Corporation under the trade designation Carbowax 8000, is used as about a 10 weight percent aqueous wettability surface agent solution to coat the circulating absorbent composition over a 20.2 minute period. The absorbent composition was then recovered from the fluidized bed chamber.

Figure 4:
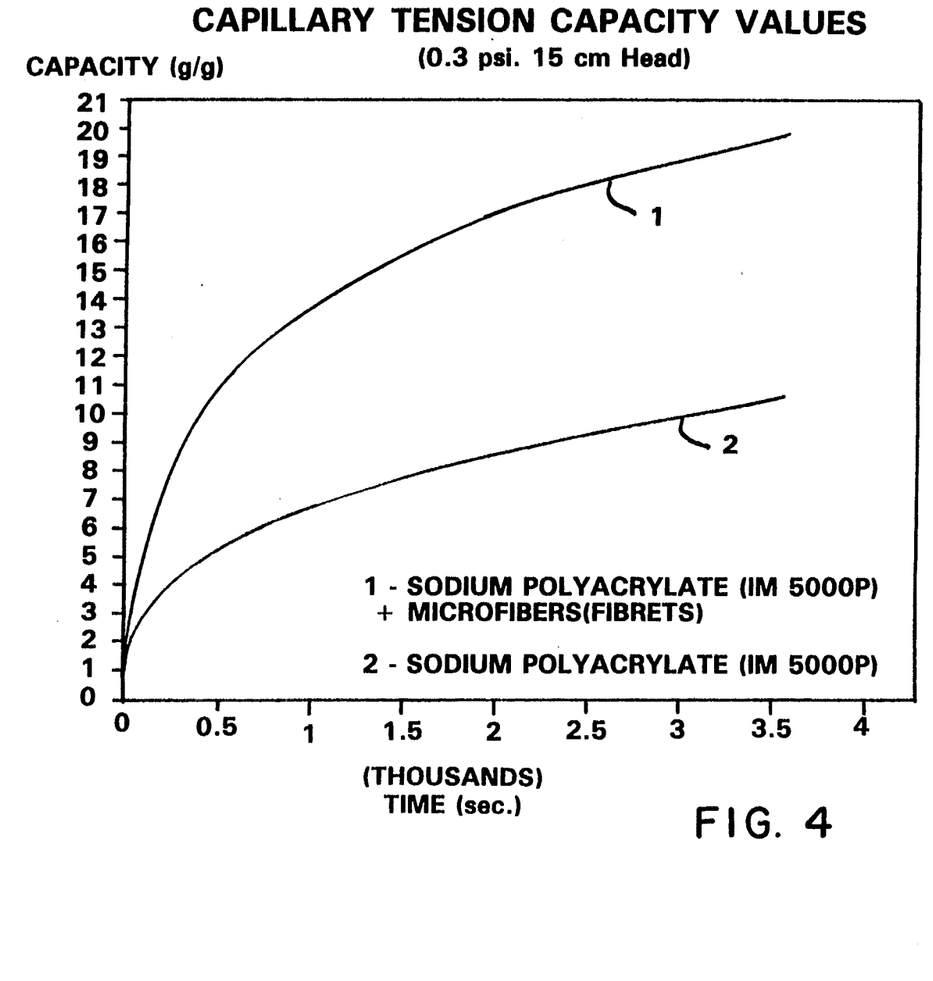
FIG. 4 is a graph summarizing data from tests on the absorbent compositions of Example 1, according to the test methods described herein.

A sample of the prepared absorbent composition was then evaluated for Capillary Tension Capacity values at a negative pressure gradient of about 15 centimeters. The results of this evaluation are shown in FIG. 4. A sample of the IM 5000P sodium polyacrylate was similarly evaluated for Capillary Tension Capacity values and the results are also shown in FIG. 4.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. An absorbent composition comprising:
   a. from about 80 to less than 100 weight percent of a hydrogel-forming polymeric material; and
   b. from about 20 to greater than 0 weight percent of a microfiber, wherein all weight percents are based on the total weight of the hydrogel-forming polymeric material and the microfiber in the absorbent composition; wherein the microfiber has a surface area between about 10 to about 25 square meters per gram of microfiber, a static charge between about $-30$ to about $-300$ volts, a fiber length to diameter ratio of at least about 50 to 1, and wherein the microfiber is attached to the hydrogel-forming polymeric material; and wherein the absorbent composition exhibits a Capillary Tension Capacity value, at a negative pressure gradient of about 15 centimeters, that is at least about 50 percent greater than the Capillary Tension Capacity value exhibited by an otherwise identical absorbent composition which does not comprise the microfiber, and wherein the absorbent composition if prepared using a fluidized bed process.

2. The absorbent composition of claim 1 wherein the hydrogel-forming polymeric material is able to absorb an amount of water at least about 10 times the weight of the hydrogel-forming polymeric material.

3. The absorbent composition of claim 1 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines.

4. The absorbent composition of claim 1 wherein the hydrogel-forming polymeric material is selected from the group consisting of carboxymethyl cellulose and alkali metal salts of polyacrylic acid.

5. The absorbent composition of claim 1 wherein the absorbent composition comprises from about 85 to about 99 weight percent hydrogel-forming polymeric material and from about 1 to about 15 weight percent microfiber, based on total weight of the hydrogel-forming polymeric material and the microfiber in the absorbent composition.

6. The absorbent composition of claim 5 wherein the absorbent composition comprises from about 85 to about 95 weight percent hydrogel-forming polymeric material and from about 5 to about 15 weight percent microfiber, based on total weight of the hydrogel-forming polymeric material and the microfiber in the absorbent composition.

7. The absorbent composition of claim 1 wherein the microfiber is selected from the group consisting of wood pulp, cellulose, cellulose acetate, cotton linter, nylon, rayon, and polyacrylonitrile fibers.

8. The absorbent composition of claim 1 wherein the microfiber has a surface area between about 15 to about 25 square meters per gram of microfiber.

9. The absorbent composition of claim 1 wherein the microfiber has a static charge between about $-50$ to about $-250$ volts.

10. The absorbent composition of claim 1 wherein the microfiber has a fiber length of less than about 1 millimeter.

11. The absorbent composition of claim 10 wherein the microfiber has a fiber length of less than about 0.5 millimeter.

12. The absorbent composition of claim 1 wherein the microfiber has a fiber diameter of less than about $5 \times 10^{-6}$ meter.

13. The absorbent composition of claim 12 wherein the microfiber has a diameter of less than about $1 \times 10^{-6}$ meter.

14. The absorbent composition of claim 1 wherein the microfiber has a length to diameter ratio of at least about 200 to 1.

15. The absorbent composition of claim 1 wherein the absorbent composition exhibits a Capillary Tension Capacity value, at a negative pressure gradient of about 15 centimeters, that is at least about 100 percent greater than the Capillary Tension Capacity value exhibited by an otherwise identical absorbent composition which does not comprise the microfiber.

16. The absorbent composition of claim 1 wherein the absorbent composition exhibits Capillary Tension Capacity value, at a negative pressure gradient of about 15 centimeters, that is at least about 200 percent greater than the Capillary Tension Capacity value exhibited by an otherwise identical absorbent composition which does not comprise the microfiber.

17. The absorbent composition of claim 1 wherein the microfiber is surface treated to be hydrophilic.

18. A disposable absorbent product comprising a liquid-permeable topsheet, a backsheet, and an absorbent structure positioned between the topsheet and the backsheet, wherein the absorbent structure comprises an absorbent composition comprising
   a. from about 80 to less than 100 weight percent of a hydrogel-forming polymeric material; and
   b. from about 20 to greater than 0 weight percent of a microfiber, wherein all weight percents are based on the total weight of the hydrogel-forming polymeric material and the microfiber in the absorbent composition; wherein the microfiber has a surface area between about 10 to about 25 square meters per gram of microfiber, a static charge between about $-30$ to about $-300$ volts, a fiber length to diameter ratio of at least about 50 to 1, and wherein the microfiber is attached to the hydrogel-forming polymeric material; and wherein the absorbent composition exhibits a Capillary Tension Capacity value, at a negative pressure gradient of about 15 centimeters, that is at least about 50 percent greater than the Capillary Tension Capacity value exhibited by an otherwise identical absorbent composition which does not comprise the microfiber, and wherein the absorbent composition is prepared using a fluidized bed process.

19. The disposable absorbent product of claim 18 wherein the hydrogel-forming polymeric material is able to absorb an amount of water at least about 10 times the weight of the hydrogel-forming polymeric material.

20. The disposable absorbent product of claim 18 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines.

21. The disposable absorbent product of claim 18 wherein the hydrogel-forming polymeric material is selected from the group consisting of carboxymethyl cellulose and alkali metal salts of polyacrylic acid.

22. The disposable absorbent product of claim 18 wherein the absorbent composition comprises from about 85 to about 99 weight percent hydrogel-forming polymeric material and from about 1 to about 15 weight percent microfibers, based on total weight of the hydrogel-forming polymeric material and the microfibers in the absorbent composition.

23. The disposable absorbent product of claim 22 wherein the absorbent composition comprises from about 85 to about 95 weight percent hydrogel-forming polymeric material and from about 5 to about 15 weight percent microfibers, based on total weight of the hydrogel-forming polymeric material and the microfibers in the absorbent composition.

24. The disposable absorbent product of claim 18 wherein the microfiber is selected from the group consisting of wood pulp, cellulose, cellulose acetate, cotton linter, nylon, rayon, and polyacrylonitrile fibers.

25. The disposable absorbent product of claim 18 wherein the microfiber has a surface area between about 15 to about 25 square meters per gram of microfiber.

26. The disposable absorbent product of claim 18 wherein the microfiber has a static charge between about $-50$ to about $-250$ volts.

27. The disposable absorbent product of claim 18 wherein the microfiber has a fiber length of less than about 1 millimeter.

28. The disposable absorbent product of claim 27 wherein the microfiber has a fiber length of less than about 0.5 millimeter.

29. The disposable absorbent product of claim 18 wherein the microfiber has a fiber diameter of less than about $5 \times 10^{-6}$ meter.

30. The disposable absorbent product of claim 29 wherein the microfiber has a diameter of less than about $1 \times 10^{-6}$ meter.

31. The disposable absorbent product of claim 18 wherein the microfiber has a length to diameter ratio of at least about 200 to 1.

32. The disposable absorbent product of claim 18 wherein the absorbent composition exhibits a Capillary Tension Capacity value, at a negative pressure gradient of about 15 centimeters, that is at least about 100 percent greater than the Capillary Tension Capacity value exhibited by an otherwise identical absorbent composition which does not comprise the microfiber.

33. The disposable absorbent product of claim 18 wherein the absorbent composition exhibits a Capillary Tension Capacity value, at a negative pressure gradient of about 15 centimeters, that is at least about 200 percent greater than the Capillary Tension Capacity value exhibited by an otherwise identical absorbent composition which does not comprise the microfiber.

34. A process for preparing an absorbent composition comprising:
   using a fluidized bed means to contact a hydrogel-forming polymeric material and a microfiber to form an absorbent composition wherein the absorbent composition comprises:
   a. from about 80 to less than 100 weight percent of a hydrogel-forming polymeric material; and
   b. from about 20 to greater than 0 weight percent of a microfiber, wherein all weight percents are based on the total weight of the hydrogel-forming polymeric material and the microfiber in the absorbent composition; wherein the microfiber has a surface area between about 10 to about 25 square meters per gram of microfiber, a static charge between about $-30$ to about $-300$ volts, a fiber length to diameter ratio of at least about 50 to 1, and wherein the microfiber is attached to the hydrogel-forming polymeric material; and wherein the absorbent composition exhibits a Capillary Tension Capacity value, at a negative pressure gradient of about 15 centimeters, that is at least about 50 percent greater than the Capillary Tension Capacity value exhibited by an otherwise identical absorbent composition which does not comprise the microfiber.

35. The process of claim 34 further comprising contacting the absorbent composition with a wettability agent effective to make the absorbent composition wettable.

36. The process of claim 35 wherein the wettability agent is polyethylene glycol.

37. The process of claim 34 further comprising contacting the hydrogel-forming polymeric material with an adhesive material.

38. The process of claim 34 comprising using an air stream to fluidize the hydrogel-forming polymeric material and the microfiber.

39. The process of claim 34 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines.

40. The process of claim 34 wherein the hydrogel-forming polymeric material is selected from the group consisting of carboxymethyl cellulose and alkali metal salts of polyacrylic acid.

41. The process of claim 34 wherein the absorbent composition comprises from about 85 to about 99 weight percent hydrogel-forming polymeric material and from about 1 to about 15 weight percent microfibers, based on total weight of the hydrogel-forming polymeric material and the microfibers in the absorbent composition.

42. The process of claim 41 wherein the absorbent composition comprises from about 85 to about 95 weight percent hydrogel-forming polymeric material and from about 5 to about 15 weight percent microfibers, based on total weight of the hydrogel-forming polymeric material and the microfibers in the absorbent composition.

43. The process of claim 34 wherein the microfiber is selected from the group consisting of wood pulp, cellulose, cellulose acetate, cotton linter, nylon, rayon, and polyacrylonitrile fibers.

44. The process of claim 34 wherein the microfiber has a fiber length of less than about 1 millimeter.

45. The process of claim 34 wherein the microfiber has a fiber diameter of less than about $5 \times 10^{-6}$ meter.

46. The process of claim 34 wherein the absorbent composition exhibits a Capillary Tension Capacity value, at a negative pressure gradient of about 15 centimeters, that is at least about 100 percent greater than the Capillary Tension Capacity value exhibited by an otherwise identical absorbent composition which does not comprise the microfiber.

47. The process of claim 34 wherein the absorbent composition exhibits a Capillary Tension Capacity value, at a negative pressure gradient of about 15 centimeters, that is at least about 200 percent greater than the Capillary Tension Capacity value exhibited by an otherwise identical absorbent composition which does not comprise the microfiber.

* * * * *